(12) United States Patent
Alruhaimi

(10) Patent No.: US 10,368,880 B1
(45) Date of Patent: Aug. 6, 2019

(54) UNIVERSAL BASE ATTACHMENT BIT AND CUTTING BIT ASSEMBLY

(71) Applicant: KING SAUD UNIVERSITY, Riyadh (SA)

(72) Inventor: Khalid Abdullah Ibrahim Alruhaimi, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/163,177

(22) Filed: Oct. 17, 2018

(51) Int. Cl.
*A61B 17/16* (2006.01)
*B23B 51/04* (2006.01)

(52) U.S. Cl.
CPC ........ *A61B 17/162* (2013.01); *A61B 17/1635* (2013.01); *A61B 17/1637* (2013.01); *B23B 51/0406* (2013.01)

(58) Field of Classification Search
CPC .................... A61B 17/1637; B23B 51/0406
See application file for complete search history.

(56) References Cited

U.S. PATENT DOCUMENTS

| 2,804,895 | A | * | 9/1957 | Clement | ............. B23B 51/0426 144/1.1 |
| 3,647,310 | A | | 3/1972 | Morse | |
| 3,837,759 | A | | 9/1974 | Bittern | |
| 5,048,379 | A | * | 9/1991 | Gramera | ................. B25B 13/06 81/121.1 |
| 5,556,399 | A | | 9/1996 | Huebner | |
| 17,934,693 | | | 5/2011 | Gillissen | |
| 2004/0161313 | A1 | | 8/2004 | Nordlin | |
| 2004/0267268 | A1 | * | 12/2004 | Gillespie | .............. A61B 10/025 606/80 |
| 2007/0269280 | A1 | | 11/2007 | Vasudeva et al. | |
| 2011/0170968 | A1 | * | 7/2011 | Moffatt | ............... B23B 51/0473 408/204 |
| 2012/0009032 | A1 | * | 1/2012 | Grussenmeyer | .... B23B 51/0426 408/204 |

* cited by examiner

*Primary Examiner* — Alan Snyder
(74) *Attorney, Agent, or Firm* — Richard C. Litman

(57) ABSTRACT

A universal base attachment bit and cutting bit assembly includes a base attachment bit and a cutting bit. The base attachment bit includes an outer threaded portion at a first end, a latch at an opposing second end, and at least one multi-sided gripping portion between the latch and the first end. The cutting bit includes a hollow cylindrical outer body and a cylindrical coupling portion within the cylindrical outer body. The cylindrical outer body includes a peripheral wall having opposed first and second open ends and a cutting edge at the first end. The coupling portion is spaced from the peripheral wall of the cylindrical body and includes an inner thread along an inner surface thereof.

6 Claims, 10 Drawing Sheets

UNIVERSAL BASE ATTACHMENT BIT AND CUTTING BIT ASSEMBLY

BACKGROUND

1. Field

The disclosure of the present patent application relates to surgical instruments, and particularly to a kit for bone harvesting and grinding, for collecting bone particulates and for mucoperiosteal tissue harvesting.

2. Description of the Related Art

Conventional surgical bone harvesting bits generally cannot be used for simultaneously cutting and grinding bone. In addition, a different tool, e.g., a hand operated handle or an electric rotary driving tool, is required for each size of the cutting bits. This leads to increased cost of the surgical set containing the different sized bits. Another disadvantage in the prior art is that the cutting bits include several rounds of helical threads for joining a cylindrical base bit and a cutting bit, and lack a proper grip to release the two attached bits. This leads to difficulty in releasing the cutting bit from its associated base bit, after completion of the procedure. The available bone grinding bits also tend to slip from the bone surface during the first rotation of the bit on the applied bone because all portions of the cylindrical bit cutting surface contact the bone simultaneously, thereby resulting in the bit slipping on the bone surface.

Thus, a universal base attachment bit and cutting bit assembly solving the aforementioned problems is desired.

SUMMARY

A universal base attachment bit and cutting bit assembly includes a base attachment bit and a cutting bit. The base attachment bit includes an outer threaded portion at a first end, a latch at an opposing second end, and at least one multi-sided gripping portion between the latch and the first end. The cutting bit includes a hollow cylindrical outer body and a cylindrical coupling portion within the cylindrical outer body. The cylindrical outer body includes a peripheral wall having opposed first and second open ends and a cutting edge at the first end. The coupling portion is spaced from the peripheral wall of the cylindrical body and includes an inner thread along an inner surface thereof for mating with the outer threaded portion of the base attachment bit.

Also provided is a kit including a base attachment bit, a plurality of cutting bits, and, optionally, an opener. Each of the cutting bits includes a coupling portion configured to be detachably attached to the base attachment bit as described above.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
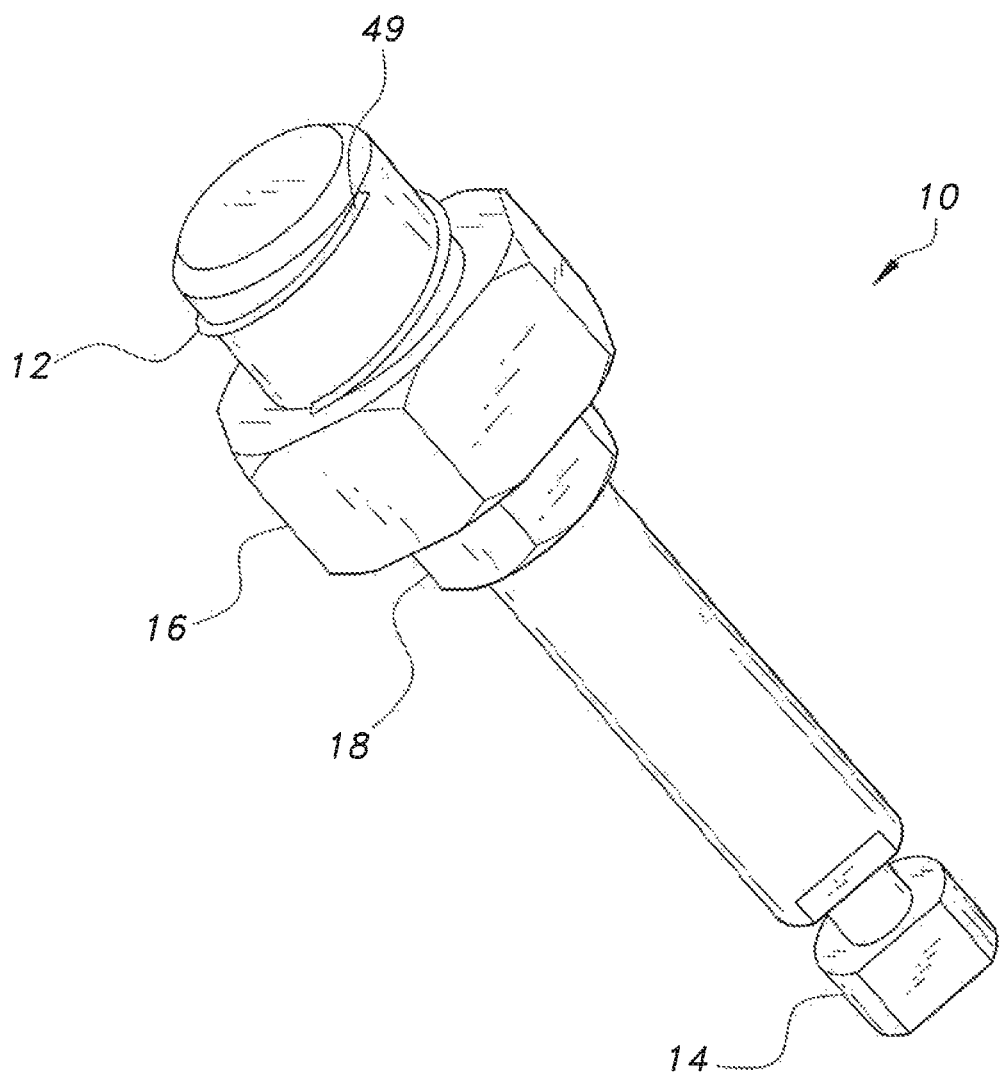
FIG. 1 is an environmental, perspective view of a bone harvesting and grinding base bit according to the present teachings.
Figure 2:
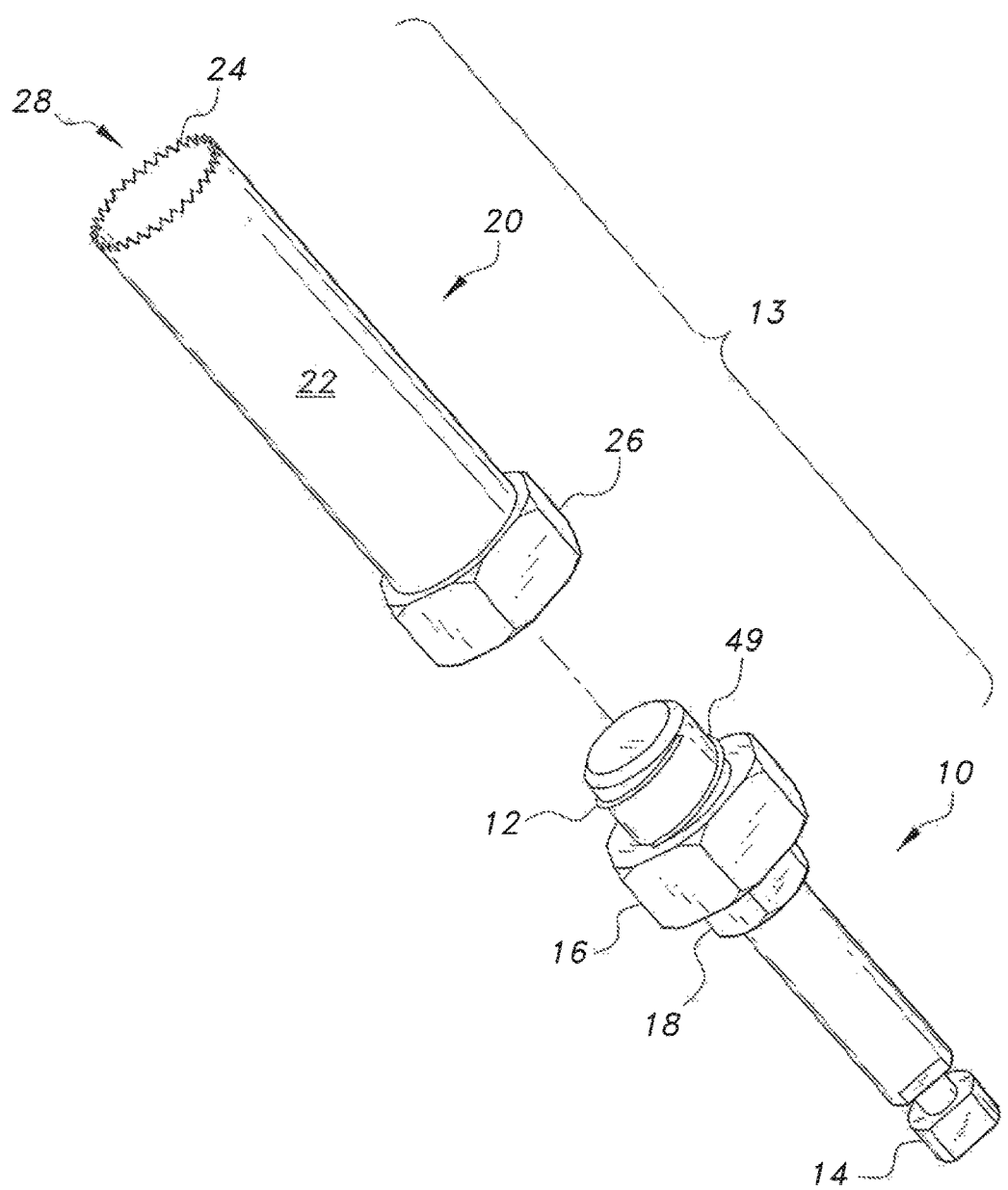
FIG. 2 is an environmental, perspective view of the universal base attachment bit and cutting bit assembly according to the present teachings.

As is shown in FIGS. 1-2, a bone harvesting and grinding base bit or universal base bit 10 includes a generally cylindrical body with external threads 12 at a first end and a latch 14 at a second end. The latch 14 can be sized and configured for attachment to an electric dental rotary driving tool (not shown), as is known in the art. The universal base bit 10 is configured to engage any one of a number of mating cutting bits to define a universal base attachment bit and cutting bit assembly 13 (FIG. 2) as described in detail herein. The base bit 10 can include at least one gripping portion 16. The gripping portion 16 includes multiple sides or angles to facilitate gripping the base bit 10 by hand, with a customized opener as described herein, or with any other appropriate tool when the base bit 10 is attached to or detached from the cutting bit 20. For example, a first hexagonal gripping portion 16 can be adjacent to the external threads 12 and a second hexagonal gripping portion 18 can be adjacent to the first hexagonal gripping portion 16. The second hexagonal gripping portion 18 can be smaller than the first hexagonal gripping portion 16. The universal base bit 10 can be used with a plurality of cutting bits that differ in size and configuration.

Figure 3:
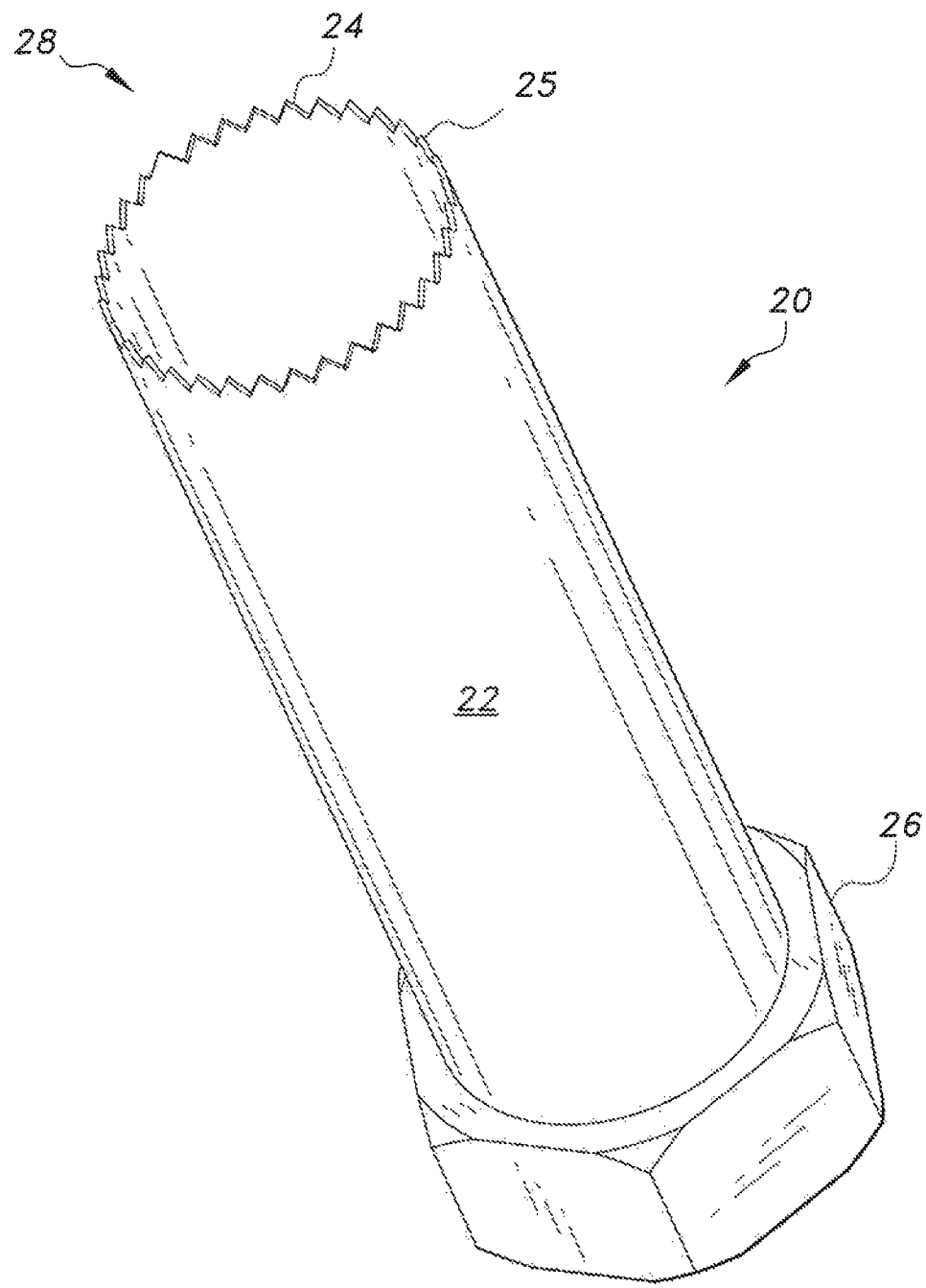
FIG. 3 is a perspective view of an exemplary cutting bit according to the present teachings.
Figure 4:
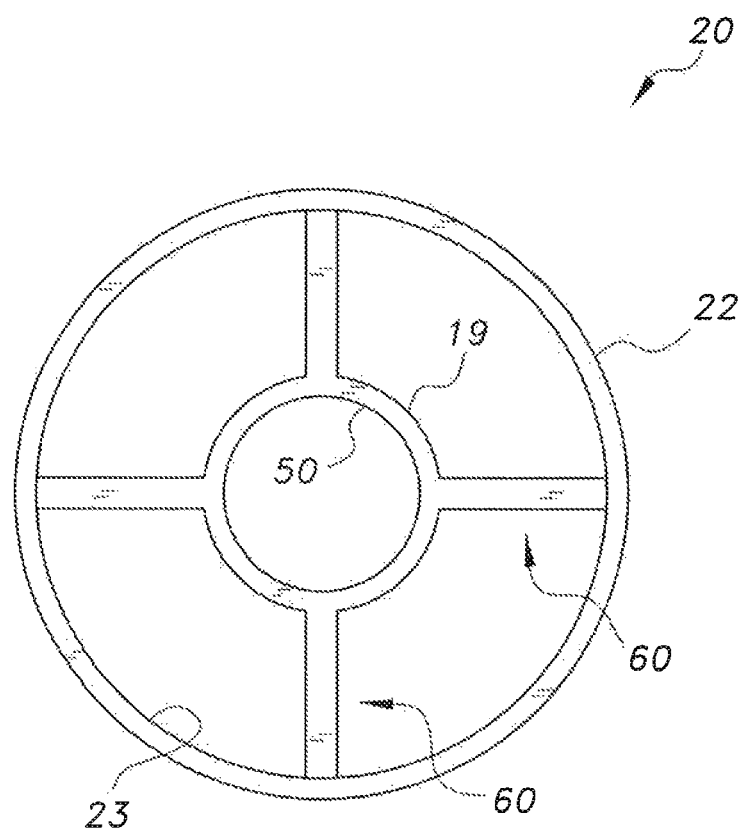
FIG. 4 is a bottom view a cutting bit according to the present teachings.

An exemplary universal base attachment bit and cutting bit assembly 13 including the base bit 10 and an exemplary cutting bit 20 is shown in FIG. 2. The cutting bit 20 has a generally hollow, tubular main body 22 with opposed first and second open ends and an inner tubular connecting or coupling portion 19 (FIG. 4) within the cylindrical body. The coupling portion 19 can be spaced from the peripheral wall of the main body 22. A circular cutting edge 24 is defined by the cylindrical body 22 at the first end. According to an embodiment, the cutting edge 24 can include a plurality of teeth 25, as shown in FIG. 3. The coupling portion 19 may include inner threads 50 defined along an inner surface thereof that are configured to engage threads 49 of the base attachment bit 10. The coupling portion 19 can be attached to the body 22 with crossbeams or ribs 60. The internal threads 50 of the coupling portion 19 are configured to detachably connect with external threads 49 of the mating universal base bit 10. Preferably, the internal threads 50 and the external threads 49 include 1 and ¼ turns or thread rounds, e.g., helical thread rounds, to allow ease in connecting and disconnecting the bits from each other, while still providing a secure connection. The latch 14 is configured for attachment to a rotary hand piece.

Figure 5A:
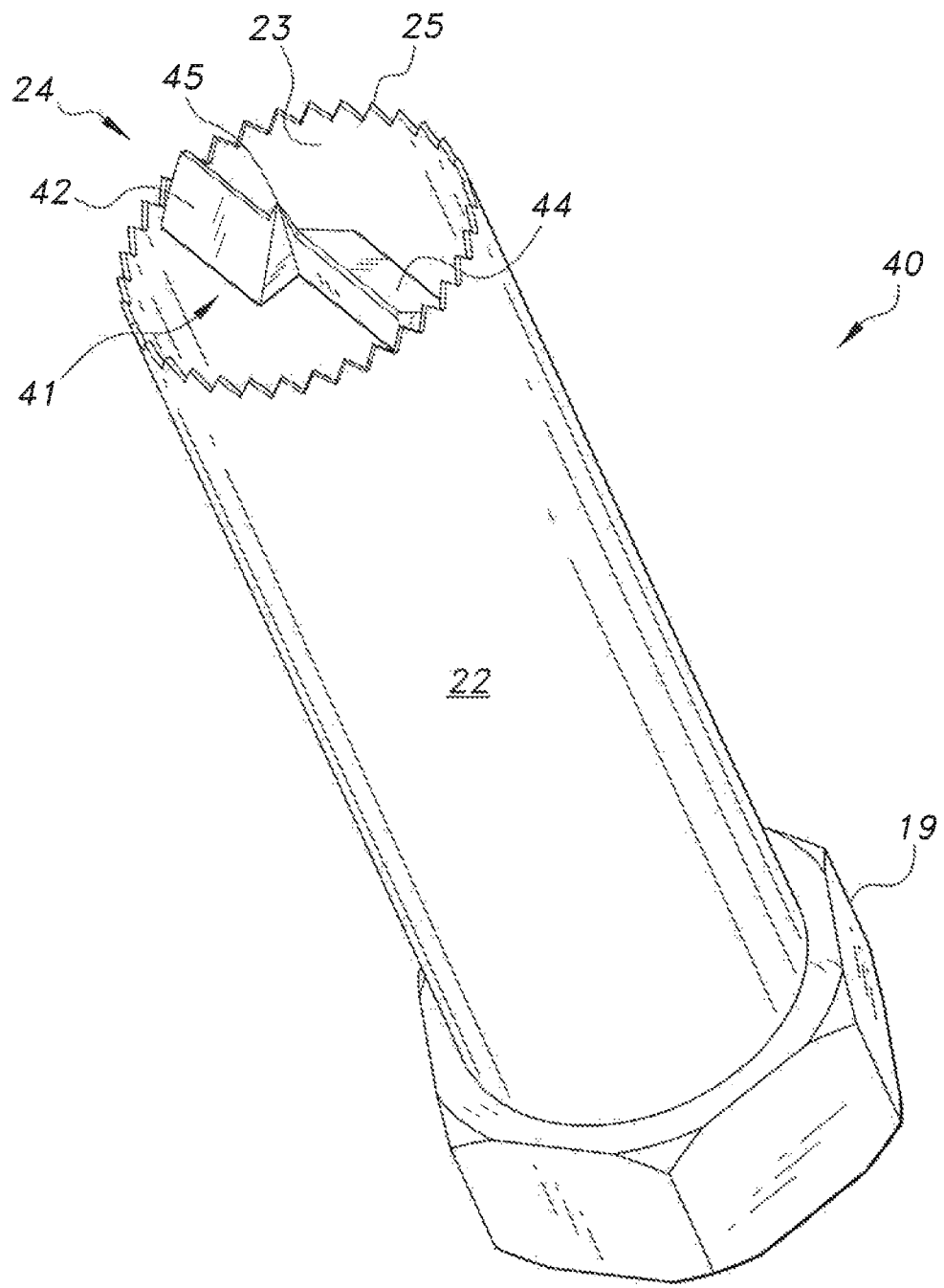
FIG. 5A is a perspective view of an alternative embodiment of the cutting bit according to the present teachings.
Figure 5B:
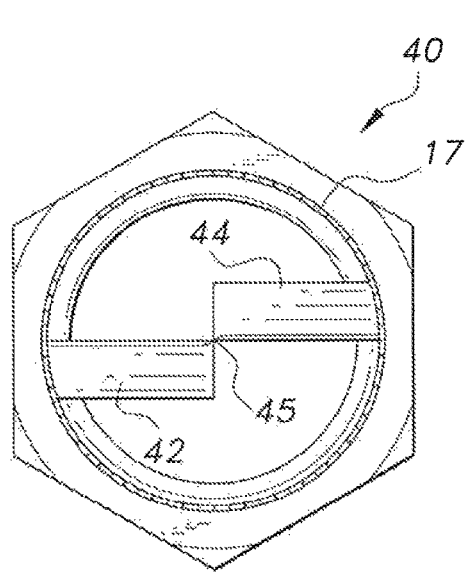
FIG. 5B is a top plan view of the cutting bit of FIG. 5A.
Figure 5C:
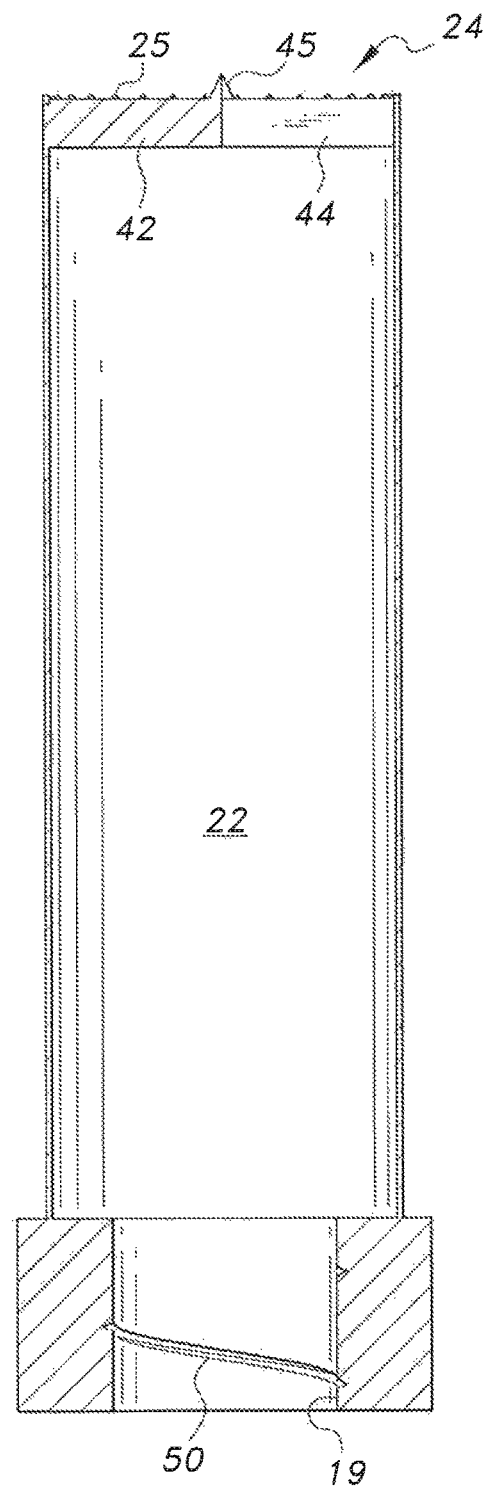
FIG. 5C is a sectional view of the cutting bit of FIG. 5A.

FIGS. 5A-5C depict an alternative embodiment of the cutting bit, generally designated 40 in the drawings. The cutting bit 40 is similar to the cutting bit 20 except that a grinding knife 41 extends across the first open end. The grinding knife 41 includes a first blade 42, a second blade 44, and a raised tip 45 between the first blade 42 and the second blade 44, as shown in FIG. 5A. The tip 45 can be a triangular projection extending between and connecting the first blade 42 and the second blade 44. The first blade 42 and the second blade 44 can be angled in opposing directions (FIG. 5B). In other words, the grinding knife 41 can have opposing beveled surfaces. As is best seen in FIG. 5C, the first blade 42 and the second blade 44 are substantially aligned with the cutting edge 24, while the tip 45 extends beyond the cutting edge 24.

Figure 6:
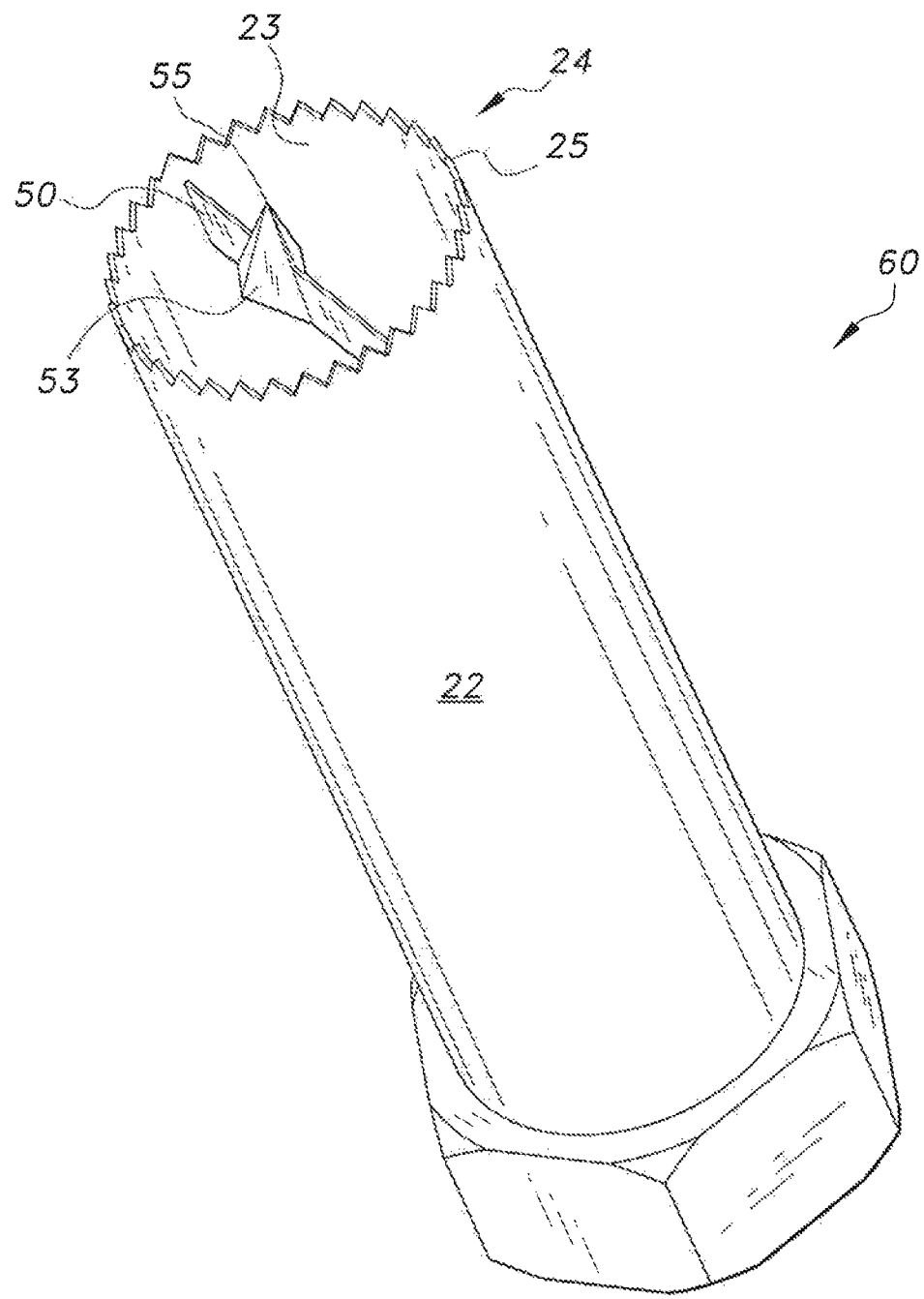
FIG. 6 is a perspective view of an alternative embodiment of the cutting bit according to the present teachings.

FIG. 6 depicts an alternative embodiment of the cutting bit, generally designated 60 in the drawings. The cutting bit 60 is similar to the cutting bit 40 except that that cutting bit 60 includes grinding knife 50 extending across the first open end. Grinding knife 50 includes a pointed head 53 extending from a central portion thereof. The head 53 can have a plurality of sloping sides that meet at a point 55. The point 55 extends beyond the cutting edge 24.

Figure 7:
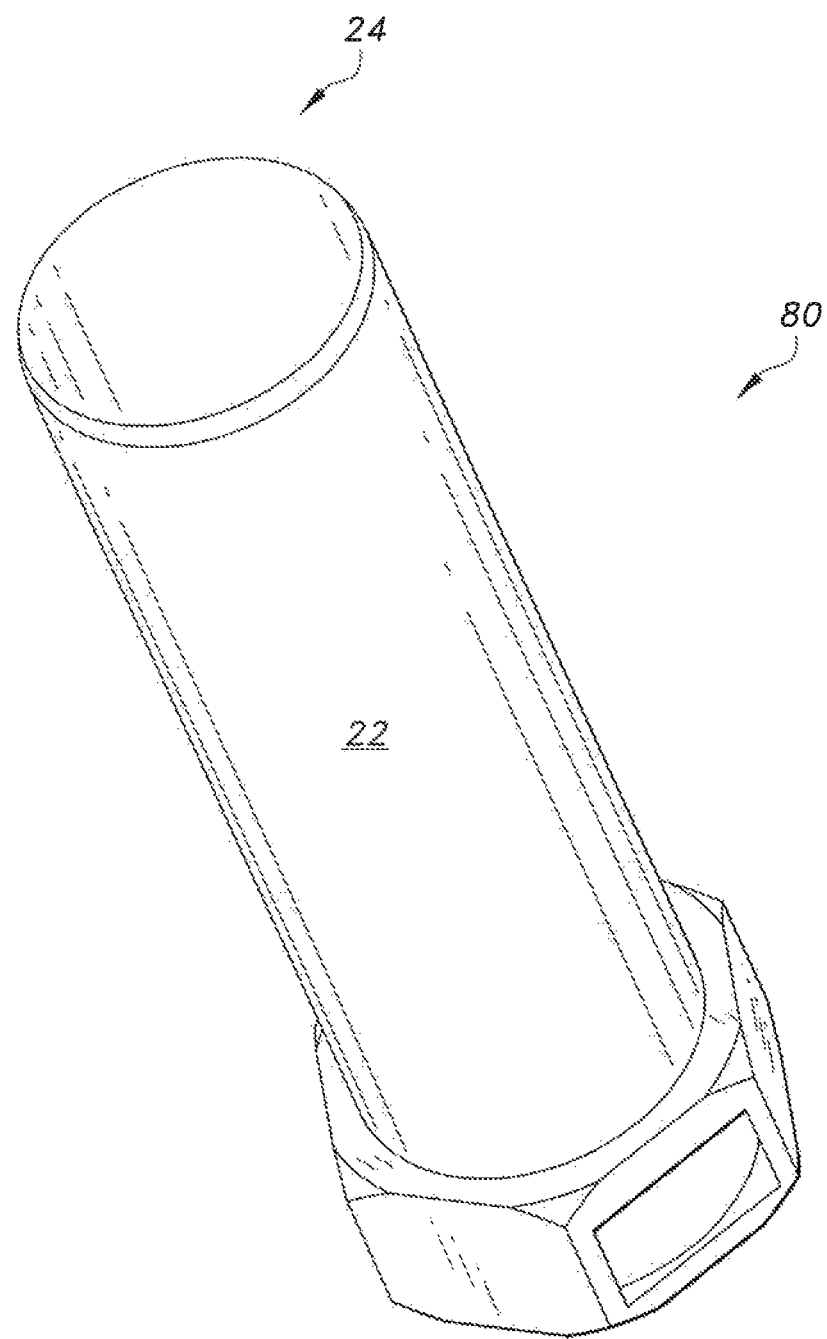
FIG. 7 is a perspective view of an alternative embodiment of the cutting bit according to the present teachings.

FIG. 7 depicts an alternative embodiment of the cutting bit, generally designated as 80 in the drawings. The cutting bit 80 is similar to the cutting bit 20 except that the cutting edge 24 is smooth and is slightly tapered inward, as shown.

Figure 8:
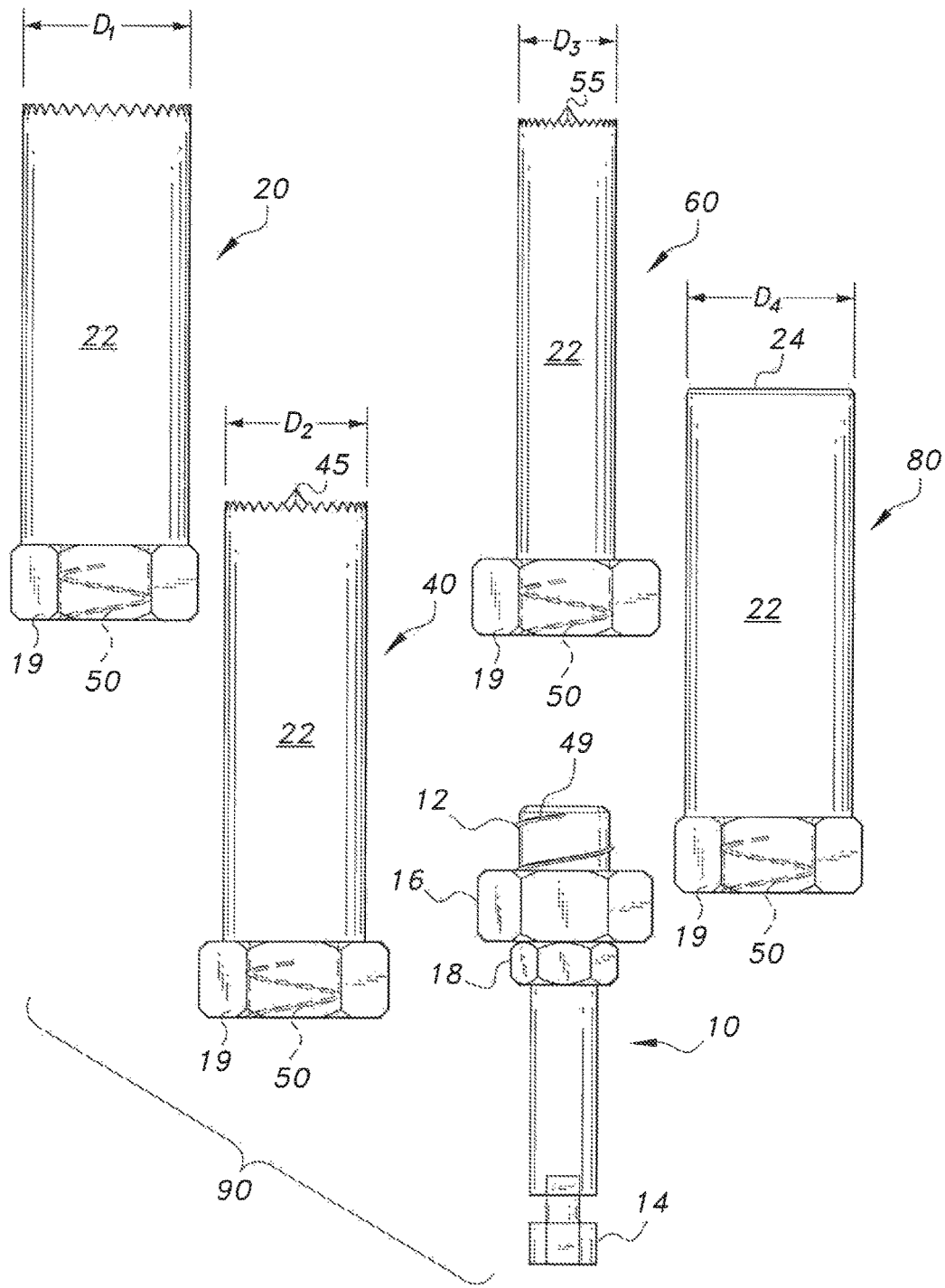
FIG. 8 is a perspective view of an exemplary kit according to the present teachings.
Figures 9A, 9B:
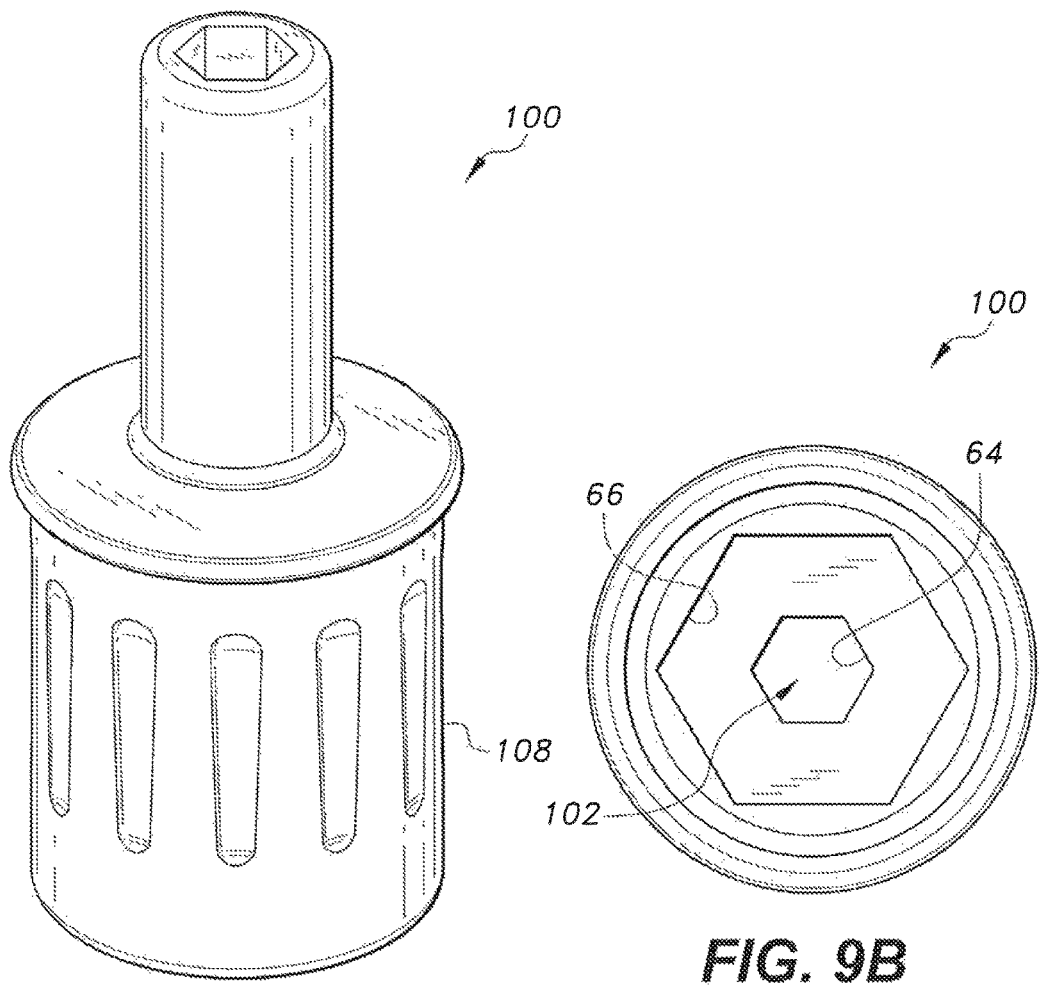
FIG. 9A is a perspective view of an opener according to the present teachings.
FIG. 9B is a top view of the opener of FIG. 9A.

Also provided is an exemplary kit 90 including a plurality of cutting bits 20, 40, 60, 80 and a base bit 10, as shown in FIG. 8. The kit 90 shown in FIG. 8 includes each of cutting bits 20, 40, 60, and 80. It should be understood, however, that a kit according to the present teachings can include only one or more than one of any of the cutting bits 20, 40, 60, and 80, and the that the cutting bit sizes can vary. In the embodiment of the kit 90 shown in FIG. 8, cutting bit 20 can have a first diameter $D_1$, cutting bit 40 can have a second diameter $D_2$, cutting bit 60 can have a third diameter $D_3$, and cutting bit 80 can have a fourth diameter $D_4$. $D_1$, $D_2$, $D_3$, and $D_4$ can be the same or different. While the diameter of the main body 22 of the different cutting bits in the kit 90 can vary, it should be understood that a diameter of the coupling portion 19 of the cutting bits and a diameter of the base bit 10 remains the same. For example, as shown in FIG. 8, all of the cutting bits have a coupling portion 19 with a size and configuration suitable for receiving and engaging the threaded end of the base bit 10. Each coupling portion 19 has an internally threaded connecting end that connects to the externally threaded mating universal base bit 10, as described above. In this way, the base bit 10 can be secured to cutting bits of various sizes. It should be understood that the bits can be provided in a wide range of sizes as is known in drill bit arts. Exemplary bit diameters include 3 mm, 5 mm, 7 mm, 9 mm, 11 mm, and 15 mm, although other diameters are possible.

The kit 90 can also include a tubular opener 100 to facilitate detaching the universal base bit 10 from the cutting bits. The opener has a central opening with first and second hexagonal inner walls 64, 66 for holding the first and second hexagonal gripping portions 16, 18 once the base bit is inserted into the central opening. A plurality of ridges 108 can extend along the outer surface of the opener to facilitate holding and twisting the opener when detaching the universal bit 10 from any one of the cutting bits 20, 40, 60, and 80. It should be understood, however, that the bits can also be detached easily by hand or with a wrench.

All components of the cutting bits and the mating universal base bit are preferably stainless steel, although other materials may be used.

In use, the universal base attachment bit and cutting bit assembly 13 is secured to an appropriate dental rotary hand piece. The tip of the cutting bit, if present, is positioned on the targeted tissue or bone site and rotation of the cutting bit is initiated. The tip is then drilled into the bone surface to secure positioning of the bit on the desired site. Continued rotation of the bit allows the cutting edge to then contact the site. Deep drilling of the bit in the bone provides a tubular hole or cavity in the bone by the cutting edge. Simultaneous grinding of the bone into fine particles can be achieved by the beveled edges of the knife.

It is to be understood that the universal base attachment bit and cutting bit assembly is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A universal base attachment bit and cutting bit assembly adapted to be secured to a rotary drill for drilling into the bone surface of a patient, consisting of:
a base attachment bit, the base attachment bit including an outer threaded portion at a first end, a latch at an opposing second end, and at least one multi-sided gripping portion between the latch and the first end; and
a plurality of cutting bits, each of the cutting bits including a hollow cylindrical outer body and a cylindrical coupling portion within the cylindrical body, the cylindrical body consisting of a peripheral wall having opposed first and second open ends and a cutting edge at the first end, wherein the cutting edge includes a plurality of teeth and a grinding knife extending entirely across the first open end, the knife including a pair of blades substantially aligned with the teeth of the cutting edge, further wherein the blades are angled with respect to one another and form a tip extending between the blades, the tip extending beyond the plurality of teeth of the cutting edge thereby adapted to be drilled into the patient's bone surface to secure positioning of the bit on the desired site, the coupling portion being spaced from the peripheral wall of the cylindrical body and including an inner thread along an inner surface thereof for mating with the outer threaded portion of the base attachment bit.

2. The universal base attachment bit and cutting bit assembly according to claim 1, wherein the base bit includes first and second hexagonal gripping portions between the first end and the second end, the first hexagonal gripping portion being larger in diameter than the second hexagonal gripping portion.

3. The universal base attachment bit and cutting bit assembly according to claim 1, wherein the inner threads of the coupling portion include 1 and ¼ helical thread rounds.

4. The universal base attachment bit and cutting bit assembly according to claim 3, wherein the outer threads of the base bit includes 1 and ¼ helical thread rounds.

5. The universal base attachment bit and cutting bit assembly according to claim 1, wherein the coupling portion is connected to the cylindrical portion by a plurality of ribs.

6. The universal base attachment bit and cutting bit assembly according to claim 1, wherein the grinding knife is made of stainless steel.

\* \* \* \* \*